(12) United States Patent
Gillis

(10) Patent No.: US 6,989,156 B2
(45) Date of Patent: Jan. 24, 2006

(54) THERAPEUTIC TREATMENTS USING THE DIRECT APPLICATION OF ANTIMICROBIAL METAL COMPOSITIONS

(75) Inventor: Scott H. Gillis, Concord, MA (US)

(73) Assignee: Nucryst Pharmaceuticals Corp., Fort Saskatchewan (CA)

(*) Notice: Subject to any disclaimer, the term of this patent is extended or adjusted under 35 U.S.C. 154(b) by 0 days.

(21) Appl. No.: 10/128,208

(22) Filed: Apr. 23, 2002

(65) Prior Publication Data

US 2003/0086977 A1 May 8, 2003

Related U.S. Application Data

(63) Continuation-in-part of application No. 09/840,637, filed on Apr. 23, 2001.
(60) Provisional application No. 60/285,884, filed on Apr. 23, 2001.

(51) Int. Cl.
*A61K 9/14* (2006.01)
*A61K 9/08* (2006.01)
*A61K 33/00* (2006.01)
*A61K 33/24* (2006.01)
*A61K 33/38* (2006.01)

(52) U.S. Cl. .................. 424/618; 424/400; 424/402; 424/404; 424/405; 424/489; 424/490; 424/600; 424/604; 424/617; 424/619; 424/630; 424/631; 424/632; 424/633; 424/634; 424/635; 424/637; 424/638; 424/641; 424/642; 424/643; 424/646; 424/649; 424/650; 424/651; 424/653; 514/492; 514/493; 514/494; 514/495; 514/499; 514/500; 514/503; 514/825; 514/886; 514/951; 514/964

(58) Field of Classification Search .............. 424/400, 424/402, 404, 405, 489, 490, 600, 604, 617–619, 424/630–635, 637–638, 641–643, 646, 649–651, 424/653; 514/492–495, 499–500, 503, 825, 514/886, 951, 964
See application file for complete search history.

(56) References Cited

U.S. PATENT DOCUMENTS

| | | |
|---|---|---|
| 3,757,786 A | 9/1973 | Smith |
| 3,800,792 A | 4/1974 | McKnight et al. |
| 3,918,446 A | 11/1975 | Buttaravoli |
| 4,059,105 A | 11/1977 | Cutruzzula et al. |
| 4,324,237 A | 4/1982 | Buttaravoli |
| 4,355,636 A | 10/1982 | Oetjen et al. |
| 4,476,590 A | 10/1984 | Scales et al. |
| 4,581,028 A | 4/1986 | Fox, Jr. et al. |
| 4,633,863 A | 1/1987 | Filips et al. |
| 4,749,572 A | 6/1988 | Ahari |
| 4,803,066 A | 2/1989 | Edwards |
| 4,828,832 A | 5/1989 | De Cuellar et al. |

(Continued)

FOREIGN PATENT DOCUMENTS

| | | |
|---|---|---|
| CA | 2242033 | 1/1999 |
| CN | 1082645 | 2/1994 |
| CN | 1241662 | 1/2000 |
| CN | 1262093 | 8/2000 |
| CN | 1279222 | 1/2001 |
| CN | 1291666 | 4/2001 |
| CN | 1291667 | 4/2001 |
| CN | 1306117 | 8/2001 |
| CN | 1322474 | 11/2001 |
| CN | 1322874 | 11/2001 |
| CN | 1328819 | 1/2002 |
| CN | 1328827 | 1/2002 |
| DE | 2748882 | 5/1979 |
| DE | 3807944 | 9/1989 |
| DE | 195 41 735 A1 | 5/1997 |
| EP | 0 136 768 | 4/1985 |
| EP | 0 254 413 | 1/1987 |
| EP | 0 356 060 | 8/1989 |
| EP | 0 355 009 | 2/1990 |
| EP | 0 378 147 | 7/1990 |

(Continued)

OTHER PUBLICATIONS

Burrell, et al. "Efficacy of Silver–Coated Dressings as Bacterial Barriers in a Rodent Burn Sepsis Model" *Wounds* 1999; 11(4): 64–71.
Demling, et al., "The Role of Silver in Wounds Healing: Effects of Silver on Wound Management," *Wounds*, vol. 13, No. 1 Jan./Feb. 2001 Supplement A; pp. 5–14.
Djokic et al., "An Electrochemical Analysis of Thin Silver Films Produced by Reactive Sputtering", *Journal of The Electrochemical Society*, 148 (3) C191–C196 (2001).
Kirsner, et al., "The Role of Silver in Wound Healing: Matrix Metalloproteinases in Normal and Impaired Wound Healing: A Potential Role of Nanocrystalline Silver," *Wounds*, vol. 13, No. 3, May/Jun. 2001, Supplement C pp. 5–12.
Olson et al., "Healing of Porcine Donor sites Covered with Silver–coated Dressings"* *Eur J Surg* 2000; 166: 486–489.
Ovington, "The Role of Silver in Wound Healing: Why is Nanocrystalline Silver Superior? Nanocrystalline Silver: Where the Old and Familiar Meets a New Frontier," *Wounds* vol. 13, No. 2, Mar/Apr. 2001, Supplement B; pp. 5–10.
Sant et al., "Novel duplex antimicrobial silver films deposited by magnetron sputtering", *Philosophical Magazine Letters*, vol. 80, No. 4, 249–256.

(Continued)

Primary Examiner—John Pak
(74) Attorney, Agent, or Firm—Fish & Richardson P.C.

(57) ABSTRACT

Therapeutic treatments using the direct application of selected structures of antimicrobial metals in free-standing powder form, solution form and/or suspension form in therapeutically effective amounts. The selected structures of antimicrobial metals serve as an antimicrobial agent, an anti-inflammatory agent, an immuno modulator agent, an enzyme modulator agent, and/or an anti-tumor agent, for human and/or animal use.

16 Claims, No Drawings

U.S. PATENT DOCUMENTS

| | | | |
|---|---|---|---|
| 4,847,049 A | 7/1989 | Yamamoto |
| 4,952,411 A | 8/1990 | Fox, Jr. et al. |
| 4,960,413 A | 10/1990 | Sagar et al. |
| 5,019,096 A | 5/1991 | Fox, Jr. et al. |
| 5,122,418 A | 6/1992 | Nakane et al. |
| 5,143,717 A | 9/1992 | Davis |
| 5,236,421 A | 8/1993 | Becher |
| 5,270,358 A | 12/1993 | Asmus |
| 5,369,155 A | 11/1994 | Asmus |
| 5,372,589 A | 12/1994 | Davis |
| 5,454,889 A | 10/1995 | McNicol et al. |
| 5,457,015 A | 10/1995 | Boston |
| 5,534,288 A | 7/1996 | Gruskin et al. |
| 5,563,132 A | 10/1996 | Bodaness |
| 5,569,207 A | 10/1996 | Gisselberg et al. |
| 5,578,073 A | 11/1996 | Haimovich et al. |
| 5,631,066 A | 5/1997 | O'Brien |
| 5,744,151 A | 4/1998 | Capelli |
| 5,770,255 A | 6/1998 | Burrell et al. |
| 5,792,793 A | 8/1998 | Oda et al. |
| 5,895,419 A | 4/1999 | Tweden et al. |
| 5,945,032 A | 8/1999 | Breitenbach et al. |
| 5,981,822 A | 11/1999 | Addison |
| 6,022,547 A | 2/2000 | Herb et al. |
| 6,071,541 A | 6/2000 | Murad |
| 6,071,543 A | 6/2000 | Thornfeldt |
| 6,123,925 A | 9/2000 | Barry et al. |
| 6,126,931 A | 10/2000 | Sawan et al. |
| 6,165,440 A | 12/2000 | Esenaliev |
| 6,187,290 B1 | 2/2001 | Gilchrist et al. |
| 6,197,351 B1 | 3/2001 | Neuwirth |
| 6,201,164 B1 | 3/2001 | Wulff et al. |
| 6,224,898 B1 | 5/2001 | Balogh et al. |
| 6,258,385 B1 | 7/2001 | Antelman |
| 6,277,169 B1 | 8/2001 | Hampden-Smith et al. |
| 6,294,186 B1 | 9/2001 | Beerse et al. |
| 6,365,130 B1 | 4/2002 | Barry et al. |
| 6,720,006 B2 | 4/2004 | Hanke et al. ............... 424/484 |
| 2001/0010016 A1 | 7/2001 | Modak et al. |
| 2002/0001628 A1 | 1/2002 | Ito |
| 2002/0016585 A1 | 2/2002 | Sachse |
| 2002/0025344 A1 | 2/2002 | Newman et al. |
| 2002/0045049 A1 | 4/2002 | Madsen |
| 2003/0170314 A1 * | 9/2003 | Burrell et al. ............... 424/618 |

FOREIGN PATENT DOCUMENTS

| | | |
|---|---|---|
| EP | 0 599 188 | 6/1994 |
| EP | 0 681 841 A1 | 11/1995 |
| EP | 0780138 | 6/1997 |
| EP | 834319 * | 4/1998 |
| EP | 1 159 972 | 12/2001 |
| GB | 420052 | 11/1934 |
| GB | 427106 | 4/1935 |
| GB | 965010 | 7/1964 |
| GB | 1270410 | 4/1972 |
| GB | 2 073 024 | 10/1981 |
| GB | 2 140 684 | 12/1984 |
| HU | 980078 A | 9/1999 |
| IT | 022309 | 12/1990 |
| JP | 60-21912 | 2/1985 |
| JP | SHO 58-126910 | 2/1985 |
| JP | 04244029 A | 9/1992 |
| JP | 11 060493 A | 3/1999 |
| JP | 11 116488 | 4/1999 |
| WO | 87/07251 | 12/1987 |
| WO | WO 89/09054 | 10/1989 |
| WO | 92/13491 | 8/1992 |
| WO | WO 96/17595 | 6/1996 |
| WO | WO 98/41095 | 9/1998 |
| WO | 98/51273 | 11/1998 |
| WO | 0030697 | 6/2000 |
| WO | 00/44414 | 8/2000 |
| WO | 00/64505 | 11/2000 |
| WO | 00/64506 | 11/2000 |
| WO | WO 00/78281 | 12/2000 |
| WO | 00/78282 | 12/2000 |
| WO | 01/15710 | 3/2001 |
| WO | 01/24839 | 4/2001 |
| WO | WO 01/26627 | 4/2001 |
| WO | 0127365 | 4/2001 |
| WO | 01/34686 | 5/2001 |
| WO | 01/41774 | 6/2001 |
| WO | 01/41819 | 6/2001 |
| WO | 01/43788 | 6/2001 |
| WO | 01/49115 | 7/2001 |
| WO | 01/49301 | 7/2001 |
| WO | 01/49302 | 7/2001 |
| WO | 01/49303 | 7/2001 |
| WO | 01/70052 | 9/2001 |
| WO | 01/74300 | 10/2001 |
| WO | 02/15698 | 2/2002 |
| WO | 02/18003 | 3/2002 |
| WO | 02/18699 | 3/2002 |
| WO | 02/44625 | 6/2002 |
| WO | 02/085299 A2 | 10/2002 |
| WO | 02/085384 A2 | 10/2002 |
| WO | 02/085385 A2 | 10/2002 |
| WO | 02/085386 A2 | 10/2002 |
| WO | 02/085387 A2 | 10/2002 |

OTHER PUBLICATIONS

Hoet, Peter H.M. et al., "Nanoparticles –known and unknown health risks," Journal of Nanobiotechnology, vol. 2, pp. 1–15, 2004.

Borm, Paul J. A. et al., "Toxicological hazards of inhaled nanoparticles–potential implications for drug delivery," Journal of Nanoscience and Nanotechnology, vol. 4(5), pp. 521–531, 2004.

Ozkan, M., "Quantum dots and other nanoparticles: what can they offer to drug discovery" ? Drug Discovery Today, vol. 9(24), pp. 1065–1071, 2004.

Williams, D., "Nanocrystalline metals: another opportunity for medical devices?" Medical Device Technology, vol. 14(9), p. 12 (pages 1–4 in the copy obtained via ProQuest), 2003.

Grier, N., Ph.D., "Silver and Its Compounds", Disinfection, Sterilization and Preservation, pp. 395–407, 1977. (S.S. Block, Lea and Febiger).

WPIDS abstract 1966–11488F (1966).

WPIDS abstract 1989–312257 (1989).

Medline abstract, accession no. 96064219 (1996).

Carrel, Thierry, "Definitive Cure of Recurrent Prosthetic Endocarditis using Silver–Coated St. Jude Medical Heart Valves: A Preliminary Case Report." *J. Heart Valve Dis*: 7:5, Sep. 1998.

* cited by examiner

THERAPEUTIC TREATMENTS USING THE DIRECT APPLICATION OF ANTIMICROBIAL METAL COMPOSITIONS

REFERENCE TO PENDING PRIOR PATENT APPLICATIONS

This patent application:

(1) claims benefit of pending prior U.S. Provisional Patent Application Ser. No. 60/285,884, filed Apr. 23, 2001 by Robert E. Burrell et al. for THERAPEUTIC TREATMENTS USING THE DIRECT APPLICATION OF NOBLE METAL COMPOSITIONS (Attorney's Docket No. WEST-1 PROV), which patent application is hereby incorporated herein by reference; and (2) is a continuation-in-part of pending prior U.S. patent application Ser. No. 09/840,637, filed Apr. 23, 2001 by Robert E. Burrell et al. for TREATMENT OF ACNE (Attorney's Docket No. 53-01), which patent application is also hereby incorporated herein by reference.

FIELD OF THE INVENTION

This invention relates to therapeutic treatments in general, and more particularly to therapeutic treatments using the direct application of antimicrobial metal compositions.

BACKGROUND OF THE INVENTION

Localized infections affect millions of people each year. If not timely treated, localized infections may spread, can result in unnecessary pain, may require increasingly more aggressive treatment, can result in developmental delays and permanent disability and, in severe cases, can even result in death.

A common form of treatment for localized infections is oral antibiotic therapy. However, this treatment is systemic, requires multiple dosages, frequently causes side effects, and can give rise to the evolution of antibiotic-resistant bacteria. Furthermore, debates are common among healthcare professionals and the general population regarding the over-use of antibiotics.

As a result, there is a significant need for an improved treatment for localized infections.

DESCRIPTION OF THE INVENTION

Overview

Nucryst Pharmaceuticals Corp. and its predecessors, all of Fort Saskatchewan, Alberta, Canada and sometimes collectively referred to herein as "Nucryst", have developed selected structures of antimicrobial metals such as silver, gold, platinum, palladium, etc. See, for example, International Patent Publication No. WO 93/23092, published Nov. 25, 1993; International Patent Publication No. WO 95/13704, published May 26, 1995; and International Patent Publication No. WO 98/41095, published Sep. 24, 1998, which documents are hereby incorporated herein by reference. These selected structures of antimicrobial metals will hereinafter sometimes be collectively referred to as "antimicrobial metals with atomic disorder".

Nucryst has determined that its antimicrobial metals with atomic disorder provide excellent therapeutic benefits. More particularly, antimicrobial metals with atomic disorder have been found to serve effectively as an antimicrobial agent, an anti-inflammatory agent, an immuno modulator agent, an enzyme modulator agent, and/or an anti-tumor agent, for human and/or animal use. Among other things, antimicrobial metals with atomic disorder have proven to be a broad spectrum (e.g., gram positive, gram negative, fungus and drug resistant) bacteriocidal agent with little likelihood of fostering resistant bacteria and having a sustained antimicrobial activity (for example, antimicrobial activity lasting over seven days has been consistently demonstrated with antimicrobial metals with atomic disorder).

Furthermore, Nucryst has recently discovered new ways of forming its antimicrobial metals with atomic disorder in free-standing powder form, solution form and suspension form. The ability to form antimicrobial metals with atomic disorder in free-standing powder form, solution form and suspension form has greatly expanded the possibilities for using these selected nanocrystalline compositions for therapeutic purposes. In particular, the ability to form antimicrobial metals with atomic disorder in free-standing powder form, solution form and suspension form has lead to the further discovery that it is possible to utilize antimicrobial metals with atomic disorder in a radical new way, i.e., for direct application to a wide range of different tissues so as to therapeutically treat a wide range of different medical disorders.

Furthermore, by combining the therapeutic benefits of antimicrobial metals with atomic disorder with recent advances in minimally invasive surgery, including small-needle and needle-less drug delivery systems, therapeutic treatments may be applied to internal anatomy as well as to surface anatomy.

Antimicrobial Metals with Atomic Disorder

The present invention utilizes selected structures of antimicrobial metals. The antimicrobial metals are preferably selected noble metals such as silver, gold, platinum, palladium, etc. The structures are formed with atomic disorder, such that ions, clusters, atoms or molecules of the metals are released at a concentration sufficient to provide a localized therapeutic effect. The structures are preferably in nanocrystalline form. Antimicrobial metals with atomic disorder may be prepared in the manner taught in International Patent Publication No. WO 93/23092, published Nov. 25, 1993; International Patent Publication No. WO 95/13704, published May 26, 1995; and International Patent Publication No. WO 98/41095, published Sep. 24, 1998, which documents are incorporated herein by reference.

As used herein, the terms and phrases set out below are intended to have the meanings as follows:

"Metal" or "metals" includes one or more metals whether in the form of substantially pure metals, alloys or compounds such as oxides, nitrides, borides, sulphides, halides or hydrides.

"Antimicrobial metals" are silver, gold, platinum, palladium, iridium, zinc, copper, tin, antimony, bismuth, or mixtures of these metals with same or other metals, silver, gold, platinum and palladium being preferred, and silver being most preferred.

"Noble metals" are silver, gold, platinum and palladium, or mixtures of such metals with same or other metals, with silver metal being the most preferred.

"Antimicrobial effect" means that atoms, ions, molecules or clusters of the antimicrobial or noble metal are released into the electrolyte which the coating contacts in concentration sufficient to inhibit microbial growth on and in the vicinity of the coating. The most common methods of measuring an antimicrobial effect are a zone of inhibition test (which indicates an inhibitory effect, whether microbiostatic or microbiocidal) or a logarithmic reduction test (which indicates a microbiocidal effect). In a zone of inhibition test (ZOI) the material to be tested is placed on a bacterial lawn (or a lawn of other microbial species) and incubated. A relatively small or no ZOI (ex. less than 1 mm) indicates a non-useful antimicrobial effect, while a larger ZOI (ex. greater than 5 mm) indicates a highly useful antimicrobial effect. The ZOI is generally reported as a corrected zone of inhibition (CZOI), wherein the size of the test sample is subtracted from the zone. A logarithmic reduction test in viable bacteria is a quantitative measure of the efficacy of an antibacterial treatment; for example, a 5 log reduction means a reduction in the number of microorganisms by 100,000-fold (e.g., if a product contained 100,000 pertinent microorganisms, a 5 log reduction would reduce the number of pertinent microorganisms to 1). Generally, a 3 log reduction represents a bactericidal effect. The logarithmic reduction test involves combining the inoculum with the test treatment, recovering the bacteria or other microbial species, and enumerating the bacteria or other microbial species using serial dilutions.

"Anti-inflammatory effect" means a reduction in one or more of the symptoms of erythema (redness), edema (swelling), pain and pruritus which are characteristic of inflammatory skin conditions.

"Inflammatory skin conditions" refers to those conditions of the skin in which inflammatory cells (e.g., polymorphonuclear neutrophils and lymphocytes) infiltrate the skin with no overt or known infectious etiology, but excluding psoriasis and its related conditions. Symptoms of inflammatory skin conditions generally include erythema (redness), edema (swelling), pain, pruritus, increased surface temperature and loss of function. As used herein, inflammatory skin conditions include, but are not limited to, eczema and related conditions, insect bites, erythroderma, mycosis fungoides and related conditions, pyoderma gangrenosum, erythema multiforme, rosacea, onychomycosis, and acne and related conditions, but excluding psoriasis and its related conditions.

"Biocompatible" means generating no significant undesirable host response for the intended utility. Most preferably, biocompatible materials are non-toxic for the intended utility. Thus, for human utility, biocompatible is most preferably non-toxic to humans or human tissues.

"Sustained release" or "sustainable basis" are used to define release of atoms, molecules, ions or clusters of a antimicrobial metal that continues over time measured in hours or days, and thus distinguishes release of such metal species from the bulk metal, which release such species at a rate and concentration which is too low to be therapeutically effective, and from highly soluble salts of antimicrobial metals such as silver nitrate, which releases silver ions virtually instantly, but not continuously, in contact with an alcohol or electrolyte.

"Atomic disorder" includes high concentrations of one or more of: point defects in a crystal lattice, vacancies, line defects such as dislocations, interstitial atoms, amorphous regions, grain and sub grain boundaries and the like relative to its normal ordered crystalline state. Atomic disorder leads to irregularities in surface topography and inhomogeneities in the structure on a nanometer scale.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Diffusion", when used to describe conditions which limit diffusion in processes to create and retain atomic disorder, i.e. which freeze-in atomic disorder, means diffusion of atoms (adatom diffusion) and/or molecules on the surface or in the matrix of the material being formed.

"Alcohol or water-based electrolyte" is meant to include any alcohol or water-based electrolyte that the antimicrobial materials of the present invention might contact in order to activate (i.e. cause the release of species of the antimicrobial metal) into same. The term is meant to include alcohols (short chain ($C_6$ or less) and preferably $C_4$ or less), water, gels, fluids, solvents, and tissues containing, secreting, or exuding water or water-based electrolytes, including body fluids (for example blood, urine, or saliva), and body tissue (for example skin).

"Bioabsorbable" as used herein in association includes substrates which are useful in medical devices, that is which are biocompatible, and which are capable of bioabsorption in period of time ranging from hours to years, depending on the particular application.

"Bioabsorption" means the disappearance of materials from their initial application site in the body (human or mammalian) with or without degradation of the dispersed polymer molecules.

"Colour change" is meant to include changes of intensity of light under monochromatic light as well as changes of hue from white light containing more than one wavelength.

An "interference colour" is produced when light impinges on two or more partly reflective surfaces separated by a distance which bears the right relationship to the wavelength of the light to be removed by destructive interference.

"Partly reflective" when used to describe the base or top layer materials, means that the material has a surface which reflects a portion of incident light, but which also transmits a portion of the incident light. Reflection occurs when a ray of incoming light encounters a boundary or interface characterized by a change in refractive index between two media. For the top layer of the antimicrobial materials of this invention, that interface is with air. For the base layer, the interface is with the top layer. The reflectance of the base and top layers is balanced so as to generate an interference colour.

"Partly light transmissive" when used to describe a thin film of the top layer material means that the thin film is capable of transmitting at least a portion of incident visible light through the thin film.

"Detectable" when used to describe a colour change means an observable shift in the dominant wavelength of the reflected light, whether the change is detected by instrument, such as a spectrophotometer, or by the human eye. The dominant wavelength is the wavelength responsible for the colour being observed.

"Cold working" as used herein indicates that the material has been mechanically worked such as by milling, grinding, hammering, mortar and pestle or compressing, at temperatures lower than the recrystallization temperature of the material. This ensures that atomic disorder imparted through working is retained in the material.

"Pharmaceutically- or therapeutically-acceptable" is used herein to denote a substance which does not significantly interfere with the effectiveness or the biological activity of the active ingredients (antimicrobial and anti-inflammatory activities) and which has an acceptable toxic profile for the host to which it is administered.

"Therapeutically effective amount" is used herein to denote any amount of a formulation of the antimicrobial or noble metals which will exhibit either or both of an antimicrobial and optionally an anti-inflammatory effect, or some other therapeutic effect, when applied to the affected area of the tissue. A single application of the formulations of the present invention may be sufficient, or the formulations may be applied repeatedly over a period of time, such as several times a day for a period of days or weeks. The amount of the active ingredient, that is the antimicrobial or noble metal in the form of a coating, powder or dissolved in liquid solution, will vary with the conditions being treated, the stage of advancement of the condition, the age and type of host, and the type and concentration of the formulation being applied. Appropriate amounts in any given instance will be readily apparent to those skilled in the art or capable of determination by routine experimentation.

"Carrier" means a suitable vehicle including one or more solid, semisolid or liquid diluents, excipients or encapsulating substances which are suitable for administration to the skin.

"Nanocrystalline" is used herein to denote single-phase or multi-phase polycrystals, the grain size of which is less than about 100, more preferably <50, even more preferably <40, even more preferably <30, and most preferably <25 nanometers in at least one dimension. The term, as applied to the crystallite or grain size in the crystal lattice of coatings, powders or flakes of the antimicrobial or noble metals, is not meant to restrict the particle size of the materials when used in a powder form.

"Powder" is used herein to include particulates of the antimicrobial or noble metals ranging from nanocrystalline (less than 100 nm) to submicron sized powders up to flakes. Preferably, powders of the antimicrobial or noble metals used in the present invention are sized at less than 100 $\mu$m, and more preferably less than 40 $\mu$m, and most preferably less than 10 $\mu$m.

"Grain size", or "crystallite size" means the size of the largest dimension of the crystals in the antimicrobial metal coating or powder.

"Hydrocolloid" means a synthetically prepared or naturally occurring polymer capable of forming a thickened gel in the presence of water and polyols (swelling agent). The swelling agent must be capable of swelling the hydrocolloid chosen in order to form the gel phase.

"Hydrogels" means a hydrocolloid swollen with water or another hydrophilic liquid which is used for absorbing or retaining moisture or water.

"Gel" means a composition that is of suitable viscosity for such purposes, e.g., a composition that is of a viscosity that enables it to be applied and remain on the skin.

When used herein and in the claims, the term "nanocrystalline antimicrobial metal" and similar terminology, such as "nanocrystalline coatings or powders" is meant to refer to antimicrobial metals formed with atomic disorder and having a nanocrystalline grain size.

Free-Standing Powder Form of Antimicrobial Metals with Atomic Disorder

Antimicrobial metals with atomic disorder may be provided in free-standing powder form in a variety of different ways.

By way of example but not limitation, in International Patent Publication No. WO 93/23092, published Nov. 25, 1993; and/or International Patent Publication No. WO 95/13704, published May 26, 1995; and/or International Patent Publication No. WO 98/41095, published Sep. 24, 1998, it was disclosed that antimicrobial metals with atomic disorder may be provided in free-standing powder form by "cold working".

Furthermore, in International Patent Publication No. WO 93/23092, published Nov. 25, 1993; and/or International Patent Publication No. WO 95/13704, published May 26, 1995; and/or International Patent Publication No. Wo 98/41095, published Sep. 24, 1998, it was disclosed that antimicrobial metals with atomic disorder may be provided in free-standing powder form by vapor deposition on a fixed element, with the deposited material thereafter being stripped off so as to yield the desired free-standing powder.

In accordance with a further aspect of the present invention, it has recently been discovered that antimicrobial metals with atomic disorder may be provided in free-standing powder form by vapor deposition on an NGRC ("next generation roll coater") apparatus. More particularly, a continuous belt is coated with antimicrobial metals with atomic disorder using vapor deposition techniques, with the antimicrobial metals with atomic disorder being scraped off the belt further down the line so as to yield the free-standing powder form of the antimicrobial metals with atomic disorder.

This last-mentioned method for making the free-standing powder form of the antimicrobial metals with atomic disorder (i.e., vapor deposition on an NGRC apparatus) is particularly advantageous, inasmuch as it can quickly and easily yield a relatively large supply of free-standing powder at a relatively low cost.

Crystalline powder forms of the antimicrobial or noble metals (particularly preferred being Ag, Au, Pt, and Pd) can be prepared as free standing powders, by coating powdered substrates, or from coatings on substrates which are then collected, for example by scraping and then sized. The powders may be prepared as pure metals, metal alloys or compounds such as metal oxides or metal salts, by vapour deposition, mechanical working, or compressing to impart the atomic disorder. The crystalline powders are formed with atomic disorder in accordance with the techniques set out above and as published in the prior patent applications of Burrell et al., see for example WO 93/23092, published Nov. 25, 1993, and WO 95/13704, published May 26, 1995. The atomic disorder will most typically be formed in the metal powders during physical vapour deposition as set out above for coatings or by mechanically imparting the disorder, such as by milling, grinding, hammering, mortar and pestle or compressing, under conditions of low temperature (i.e., temperatures less than the temperature of recrystallization of the material) to ensure that annealing or recyrstallization does not take place.

Alternatively, the powders may be formed by inert-gas condensation techniques, which are modified to provide atomic disorder in the powder produced, as taught in WO 95/13704 to Burrell et al.

Powders of the antimicrobial or noble metals are preferably formed by physical vapour deposition (PVD) onto a substrate such as a cold finger, a silicon wafer, solid plates, a rotating cylinder, a continuous belt in a roll coater, or on steel collectors in known PVD coaters. Preparation of powders of the present invention by sputtering onto a continuous belt in a roll coater, or other some other moving or rotating substrate surface is particularly advantageous, inasmuch as it can quickly and easily yield a relatively large supply of free-standing powder at a relatively low cost. A stainless steel belt can be used in the roll coating process without the need to provide additional cooling of the substrate. The powders or coatings are then scraped off to form a powder, and may be sized to avoid overly large particulates. The powders are scraped off the moving surface with scrapers which contact the moving surface at an angle sufficient to remove the coating in flake or powder form. The coating may be scraped off with scrapers angled for forward cutting of the coating from the moving surface, or with scrapers which remove the coating from the moving surface by reverse dragging action on the surface. The scrapers may be suspended above the belt, and either weighted or spring loaded to apply pressure sufficient to remove the coating from the moving surface. With a continuous belt, the scrapers can conveniently be located above the end rollers to remove the coating with a reverse dragging action as the belt rounds the end roller.

Alternatively, the powders of the antimicrobial or noble metals may be formed on powdered substrates which are biocompatible, or otherwise compatible for the end use of the powder. Particularly preferred powdered substrates are hydrocolloids, particularly those which are bioabsorbable and/or hygroscopic powders such as chitin. Exemplary bioabsorbable and/or hygroscopic powders are composed of:

Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers.

Naturally Derived Polymers: Proteins: albumin, fibrin, collagen, elastin; Polysaccharides: chitosan, alginates, hyaluronic acid; and Biosynthetic Polyesters: 3-hydroxybutyrate polymers.

The powders may be incorporated into or onto medical dressings or pharmaceutical formulations, by any methods known in the art. For example, the powders may be layered onto the substrates (dressings or powders), mechanically fixed within the fibres of the dressings, impregnated into dressings by physical blowing, or added to topical pharmaceutical ingredients.

Preferably, powders of the present invention are sized at less than 100 $\mu$m, and more preferably less than 40 $\mu$m, and most preferably about 3–5 $\mu$m in size.

Once antimicrobial metals with atomic disorder have been provided in free-standing powder form, they can then be used therapeutically in that form, or the free-standing powder can be used to form solutions or suspensions of the antimicrobial metals with atomic disorder prior to being used to therapeutically treat tissue.

Use of Antimicrobial Metals with Atomic Disorder in Free-standing Powder Form

Antimicrobial metals with atomic disorder in free-standing powder form may be sprinkled lightly onto surface anatomy (e.g., the skin) in therapeutically effective amounts so as to provide an antimicrobial treatment to that surface anatomy, e.g., to an infected cut. If desired, antimicrobial metals with atomic disorder may be mixed with one or more other materials prior to being sprinkled onto the skin, where these other materials may be biologically active materials (e.g., growth promoters) or biologically neutral materials acting as a "filler" to facilitate easier deployment of relatively small quantities of antimicrobial metals with atomic disorder.

Or antimicrobial metals with atomic disorder in free-standing powder form can be applied to the lungs using a so-called dry powder inhaler.

Antimicrobial metals with atomic disorder in free-standing powder form may also be injected, by small-needle or needle-less injection, into the interior of the body in therapeutically effective amounts so as to provide their therapeutic benefit to interior anatomy.

The antimicrobial metals with atomic disorder can be delivered to interior anatomy via a small-needle drug delivery system or via a needle-less drug delivery system. Such systems are available from Powderject Research Limited of Oxford, United Kingdom (see, for example, U.S. Pat. Nos. 5,899,880; 6,010,478 and 6,013,050, which patents are hereby incorporated herein by reference) and Bioject, Inc. of Portland, Oreg. (see, for example, U.S. Pat. Nos. 4,596,556; 4,790,824; 5,064,413; 5,312,335; 5,383,851; 5,399,163; 5,520,639; 6,096,002; and Des. 349,958, which patents are also hereby incorporated herein by reference). Delivery of antimicrobial metals with atomic disorder with such drug delivery systems provides local therapy to the interior anatomy.

Where the antimicrobial metals with atomic disorder are to be applied to the tissue in free-standing powder form by inhalation and/or injection, it is preferred that the particulate size be less than 2 microns, and preferably less than 1 micron, so as so minimize any adverse reaction to the presence of the particulate in the tissue.

Many health afflictions can be addressed by delivering antimicrobial metals with atomic disorder, in free-standing powder form, to an interior anatomical site with small-needle and/or needle-less drug delivery systems. Examples of some of these applications include: (1) dermal drug delivery for skin conditions such as, but not limited to, acne, psoriasis, eczema and skin infections; (2) localized infections such as, but not limited to, middle ear infections, endocarditis, pericarditis, prostatitis, sinusitis, osteomyelitis and onychomycosis; (3) mouth, gum and throat afflictions; (4) arthritis; and (5) direct-to-tumor chemotherapeutic delivery.

For example, antimicrobial metals with atomic disorder may be injected directly into psoriatic plaques. Or antimicrobial metals with atomic disorder may be injected by small-needle or needle-less injection through the eardrum (i.e., through the tympanic membrane) into the middle ear, whereby to provide a localized antimicrobial, anti-inflammatory treatment for middle ear infections. Or long-acting antimicrobial metals with atomic disorder may be injected into the prostate gland for difficult-to-treat prostate infections. And antimicrobial metals with atomic disorder may be injected into the tissues of the oral cavity and throat to treat sore throats, thrush (candida infections) and periodontal diseases such as gingivitis. Also, antimicrobial metals with atomic disorder may be injected into arthritic joints to reduce destructive inflammation. And long-acting antimicrobial metals with atomic disorder of platinum can be injected into tumors that are responsive to chemotherapy with platinum compounds.

Numerous advantages are achieved by delivering antimicrobial metals with atomic disorder to the interior anatomy using such drug delivery systems. For one thing, local treatment (versus systemic treatment) results in lower total doses being required and in fewer side effects. For another thing, the broad spectrum antimicrobial activity of the antimicrobial metals with atomic disorder results in faster infection fighting with low likelihood of bacterial resistance. Furthermore, due to the long-acting nature of the antimicrobial metals with atomic disorder, a single dose or relatively infrequent (e.g., weekly) doses results in an easier therapy regimen than many conventional treatment regimens.

Solutions of Antimicrobial Metals with Atomic Disorder

It is also possible to provide antimicrobial metals with atomic disorder in solution form. The solution form of antimicrobial metals with atomic disorder can be advantageous in many anatomical applications, since there is substantially no particulate present which might irritate tissue.

Antimicrobial metals with atomic disorder may be provided in solution form in a variety of different ways.

In one form of the invention, a solution of antimicrobial metals with atomic disorder is created by dissolving a free-standing powder of antimicrobial metals with atomic disorder in water. The free-standing powder of antimicrobial metals with atomic disorder may be packaged in a "tea-bag" type pouch, such that undissolved antimicrobial metals with atomic disorder remain captured within the pouch.

In another form of the invention, a solution of antimicrobial metals with atomic disorder may be provided by immersing, in water, a substrate carrying deposited antimicrobial metals with atomic disorder. By way of example, a carrier strip may be coated with antimicrobial metals with atomic disorder by vapor deposition, and then the carrier strip may be immersed in water so as to create the solution of antimicrobial metals with atomic disorder. Alternatively, a bandage may be coated with antimicrobial metals with atomic disorder by vapor deposition, and then the bandage may be immersed in water so as to create the solution of antimicrobial metals with atomic disorder.

The solution of antimicrobial metals with atomic disorder may be prepared in advance (e.g., at a manufacturing plant) or on site at the time of use. Where a solution of antimicrobial metals with atomic disorder is prepared in advance (e.g., at a manufacturing plant), it is preferred that the solution be created by immersing a "tea-bag" type pouch of the free-standing powder form of antimicrobial metals with atomic disorder in water and leaving it there until the time of use, or by immersing a substrate carrying deposited antimicrobial metals with atomic disorder in water and leaving it there until the time of use.

Once a solution of antimicrobial metals with atomic disorder has been created, it may be applied to tissue as a liquid or as an aerosol.

Regardless of how the solution of antimicrobial metals with atomic disorder is applied to tissue, the dosage is dependent, to at least some extent, on the concentration of antimicrobial metals with atomic disorder present in the solution. Thus, where it is necessary to apply a strong dose of antimicrobial metals with atomic disorder, it may be desirable to raise the concentration of antimicrobial metals with atomic disorder in the solution. In this respect it has been discovered that by lowering the pH of the solution, a higher concentration of antimicrobial metals with atomic disorder can be obtained and, significantly, the antimicrobial metals with atomic disorder go into solution faster. The pH of the solution can be lowered by adding acid to the solution. In one preferred form of the invention, $CO_2$ is added to the solution: the $CO_2$ creates carbonic acid, thus lowering the pH of the solution and increasing the concentration of antimicrobial metals with atomic disorder in the solution.

As noted above, once a solution of antimicrobial metals with atomic disorder has been created, it may be applied to tissue as a liquid or as an aerosol.

Use of Antimicrobial Metals with Atomic Disorder in Solution Form—Liquid Application A solution of antimicrobial metals with atomic disorder may be applied, in liquid form, and in various viscosities, to a wide range of different tissues in therapeutically effective amounts so as to therapeutically treat a wide range of different medical disorders.

By way of example, a solution of antimicrobial metals with atomic disorder can be applied as a rinse or bath or wash to treat a dermal condition such as, but not limited to, acne, psoriasis, eczema and skin infections. Alternatively, a solution of antimicrobial metals with atomic disorder can be applied as a rinse or bath or wash to treat a wound or a surgical site.

Or a solution of antimicrobial metals with atomic disorder can be applied to mouth tissue (e.g., the gums) as an oral rinse.

Or a solution of antimicrobial metals with atomic disorder can be applied to throat tissue as a gargle.

Or a solution of antimicrobial metals with atomic disorder can be applied to nasal passages and the sinus, e.g., to treat sinusitis and allergic rhinitis.

Or a solution of antimicrobial metals with atomic disorder can be applied to the eyes as eyedrops.

Or a solution of antimicrobial metals with atomic disorder can be applied to the ears as ear drops.

It is also possible to apply a solution of antimicrobial metals with atomic disorder, in liquid form, to internal anatomy using a small-needle and/or needle-less drug delivery systems, including catheter-based drug delivery systems. Thus, for example, a solution of antimicrobial metals with atomic disorder may be introduced by catheter into the bladder to treat a bladder infection; or injected into the middle ear to treat middle ear infections; or injected or instilled or otherwise introduced into the abdomen to treat a post-surgical abdominal abscess or to treat an infection from peritoneal dialysis; or injected or instilled or otherwise introduced into other internal anatomical structures, including body cavities, so as to treat conditions such as, but not limited to, endocardititis, pericarditis, prostatitis, sinusitis, osteomyelitis and onychomycosis; or injected into skin tissue to treat acne, psoriasis, eczema and/or or other skin conditions; etc.

Use of Antimicrobial Metals with Atomic Disorder in Solution Form—Aerosol Application A solution of antimicrobial metals with atomic disorder may also be applied, in aerosol form, to a wide range of different tissues in therapeutically effective amounts so as to therapeutically treat a wide range of different medical disorders.

By way of example, a solution of antimicrobial metals with atomic disorder may be applied in aerosol form to surface tissues as a spray. Thus, a solution of antimicrobial metals with atomic disorder can be applied as a spray to treat a dermal condition such as, but not limited to, acne, psoriasis, eczema and skin infections. Alternatively, a solution of antimicrobial metals with atomic disorder can be applied as a spray to treat or clean a wound or a surgical site.

By way of further example, a solution of antimicrobial metals with atomic disorder, in aerosol form, may be inhaled by a patient for deployment to the throat, the nasal and sinus passages and/or the lungs.

The aerosol of antimicrobial metals with atomic disorder may be created by passing a liquid solution of antimicrobial metals with atomic disorder through a mechanical mister (e.g., a simple spray bottle or nebulizer) and may be applied directly (e.g., via a hand inhaler) or through some other delivery system (e.g., an oxygen tent, etc.).

With respect to an aerosol of antimicrobial metals with atomic disorder, it should be appreciated that the droplet size of the aerosol can be important, for at least two reasons.

First, the droplet size of the aerosol can affect the dosage of antimicrobial metals with atomic disorder being applied to the tissue, i.e., a larger droplet size results in delivery of more antimicrobial metals with atomic disorder to the tissue.

Second, the droplet size of the aerosol can also affect delivery of the antimicrobial metals with atomic disorder to the target tissue, e.g., where the aerosol is inhaled through the mouth, big droplets tend to stay in the throat whereas small droplets (e.g., approximately 10 microns or so) tend to travel to the lungs.

Thus, depending on the dosage required and the target tissue, it may be important to regulate the droplet size of the aerosol.

In this respect, it has been found that droplet size can be regulated, to at least some extent, by the device (e.g., the mechanical mister) which is used to produce the aerosol.

In addition, it has also been discovered that the aerosol's droplet size can be adjusted, to at least some extent, by modifying the surface tension of the solution. More particularly, the solution of antimicrobial metals with atomic disorder has water as its solvent, and water has a relatively high surface tension, so it is relatively straightforward to create an aerosol having a relatively small droplet size. In accordance with the present invention, it has also been discovered that surfactants can be added to the solution so as to reduce the surface tension of the solution, whereby to create an aerosol having a relatively large droplet size. By way of example, such surfactants may comprise phospholipids, e.g., lecithin, sphingomyelin, etc.

Suspensions of Antimicrobial Metals with Atomic Disorder

It is also possible to provide antimicrobial metals with atomic disorder in suspension form. The suspension form of antimicrobial metals with atomic disorder can be advantageous in many applications, since it has a relatively long storage life and, perhaps even more importantly, has a relatively long-lasting therapeutic life.

Antimicrobial metals with atomic disorder may be provided in suspension form in a variety of different embodiments. More particularly, a suspension of antimicrobial metals with atomic disorder can be created in free-standing form or as a dried gel applied to a medical device.

Thus, in one form of the invention, a suspension of antimicrobial metals with atomic disorder can comprise a free-standing form, i.e., it can comprise a liquid such as a lotion; or a semi-solid such as a gel (i.e. a water-based hydrocolloid) or an emulsion (i.e., an oil-in-water or water-in-oil suspension) such as a cream or ointment. Formulations can include carboxymethyl cellulose ("CMC"), polyvinyl alcohol, methyl parabin, proply parabin, and 0.1% antimicrobial metals with atomic disorder in powder form.

In another form of the invention, a suspension of antimicrobial metals with atomic disorder can comprise a dried gel applied to a medical device. In this embodiment, a hydrated form of the gel is created, applied to a medical device, and then dehydrated. During use, the gel becomes rehydrated, whereby the antimicrobial metals with atomic disorder are released to provide their therapeutic effect to tissue.

Regardless of whether the suspension is free-standing or a dried gel applied to a medical device, the suspension may also include biologically active agents such as cytoconductive agents, etc. By way of example, betaglucan, a complex carbohydrate which appears to have cytoconductive properties, may be added to the suspension.

Of course, when formulating the suspension, care must be taken to avoid generating a blend which might deactivate the therapeutic effect of the antimicrobial metals with atomic disorder. Thus, for example, glycerol can be deleterious to the therapeutic effect of the antimicrobial metals with atomic disorder, and should be avoided.

Use of Antimicrobial Metals with Atomic Disorder in Suspension Form—Free-Standing Form As noted above, a suspension of antimicrobial metals with atomic disorder can comprise a free-standing form, i.e., it can comprise a liquid such as a lotion; or a semi-solid such as a gel (i.e. a water-based hydrocolloid) or an emulsion (i.e., an oil-in-water or water-in-oil suspension) such as a cream or ointment. These free-standing forms of the suspension are intended to be applied topically to the tissue which is to be treated, in therapeutically effective amounts, and can be used to treat a dermal condition such as, but not limited to, acne, psoriasis, eczema and skin infections. Alternatively, the free-standing forms of the suspension can be applied topically to treat a wound or a surgical site, etc.

Use of Antimicrobial Metals with Atomic Disorder in Suspension Form—Dried Gel

It is also possible to provide a suspension of antimicrobial metals with atomic disorder in the form of a dried gel applied to medical devices. The hydrated form of the gel is created, applied to a medical device (e.g., during manufacture of the medical device), and then dehydrated. During use, the gel becomes rehydrated, whereby the antimicrobial metals with atomic disorder are released in therapeutically effective amounts so as to provide their therapeutic effect to tissue.

Examples of medical devices which are prime candidates for a dried gel coating include catheters (e.g., urological catheters, in-dwelling catheters, drainage catheters, etc.), bone screws, total joints, vascular grafts, hernia meshes, surgical dressings, surgical packing materials, etc.

In this respect it should be appreciated that the dried gel can be quite stable and easy to handle when dehydrated, but very slippery when rehydrated. Thus, dried gels can be particularly advantageous with certain types of medical devices which might otherwise require lubrication during use, since the rehydrated gel automatically provides such lubrication. Urological catheters are one example of a medical device which generally requires lubrication during use, and which would benefit from the natural lubrication provided by the rehydrated gel.

It is also possible to provide a dried gel which is less slippery, or even non-slippery, when rehydrated.

EXAMPLE 1

6 milligrams of antimicrobial metals with atomic disorder, in free-standing powder form, are sprinkled lightly onto 6.5 $cm^2$ of burned tissue, and thereafter wet with a light spray of water or wound exudate or TDWL (Trans Dermal Water Loss) or other bodily fluids, so as to provide an antimicrobial treatment to the burned tissue. The treatment is repeated every 24 hours until the therapeutic effects are no longer needed.

EXAMPLE 2

0.5 milligrams of antimicrobial metals with atomic disorder, in free-standing powder form, are injected, using a small-needle drug delivery system or a needle-less drug delivery system, into gum tissue so as to treat gingivitis. The treatment is repeated every 3 days until the therapeutic effects are no longer needed.

EXAMPLE 3

A solution of antimicrobial metals with atomic disorder is prepared by dissolving 6 milligrams of antimicrobial metals with atomic disorder in 1 gram of water. The solution of antimicrobial metals with atomic disorder is applied as a rinse or bath or wash to a wound site so as to provide an antimicrobial treatment to the wound site. The treatment is repeated every 24 hours until the therapeutic effects are no longer needed.

EXAMPLE 4

A solution of antimicrobial metals with atomic disorder is prepared by dissolving 6 milligrams of antimicrobial metals with atomic disorder in 1 gram of water. The solution of antimicrobial metals with atomic disorder is applied to the interior of the bladder via a catheter so as to provide antimicrobial treatment to the bladder. The treatment is repeated every 8 hours until the therapeutic effects are no longer needed.

EXAMPLE 5

A solution of antimicrobial metals with atomic disorder is prepared by dissolving 6 milligrams of antimicrobial metals with atomic disorder in 1 gram of water. The solution of antimicrobial metals with atomic disorder is injected (using a small-needle or needle-less injection system) under the toenails or into the nail bed and/or the surrounding tissue of a person suffering from onychomycosis so as to provide an antimicrobial treatment to the tissue. The treatment is repeated 2 times a day until the therapeutic effects are no longer needed.

EXAMPLE 6

Summary

Solutions of nanocrystalline noble metals were prepared by immersing Acticoat® burn dressings (distributed by Smith & Nephew) in reverse osmosis water that had been pretreated with $CO_2$ in order to reduce the pH. Two different concentrations of antimicrobial metals with atomic disorder solutions were prepared by this method, the concentrations being 85 $\mu$g/mL and 318 $\mu$g/mL. Solutions of silver nitrate were also prepared to use as comparisons in the experiments. The concentrations of the silver nitrate were 103 ppm of silver and 295 ppm of silver as determined by Atomic Absorption Spectroscopy.

The solutions were in turn placed in an ultrasonic nebulizer that created small droplets containing dissolved and suspended parts of the solution of nanocrystalline noble metals. The output from the nebulizer was directed into a chamber made from a stainless steel frame and base. Petri dishes containing Mueller Hinton agar streaked with 4 h old cultures of *Pseudomonas aerugiona* and *Staphylococcus aureus* were exposed to nanocrystalline noble metal aerosols and the silver nitrate aerosols.

The results of the tests show that nanocrystalline noble metal aerosols transmit the antimicrobial activity of the dressings to remote sites, and nanocrystalline noble metal aerosols are more effective than comparable concentrations of silver nitrate.

Introduction

In many instances the delivery of antimicrobial materials may most expeditiously be accomplished by using aerosols (e.g., in the treatment of pneumonia). The drawback of aerosols is the requirement for a high concentration of the active ingredient to ensure that a sufficient amount is delivered to achieve the biological effect desired without causing problems with the carrier solvent (e.g., water). The essential requirement of the equipment for producing an aerosol that contains dissolved and suspended components of antimicrobial metals with atomic disorder is that it must form droplets of aerosol directly from the liquid form, and the aerosol droplets must be small enough to reach the lungs. This means that the droplets should be preferably less than approximately 10 $\mu$m. To meet these requirements, the aerosol cannot be created by first evaporating the liquid and then condensing it to form droplets, since this would remove the desired antimicrobial metals with atomic disorder from the aerosol. There are two methods that can be used to relatively easily form the droplets directly: (1) mechanical disruption of the liquid; and (2) air, under pressure, passing through some form of orifice that combines the air and the liquid in a way that creates droplets instead of evaporating the liquid.

Several experiments were carried out with antimicrobial metals with atomic disorder and silver nitrate solutions to determine if the antimicrobial activity of the dressing could be transferred through a direct droplet aerosol to a Petri dish.

Equipment

The method used to create an aerosol for these tests was the mechanical method in the form of an ultrasonic nebulizer. For convenience, an ultrasonic humidifier was used. The liquid containing the dissolved and suspended antimicrobial metals with atomic disorder was placed in the water reservoir of the humidifier. When power was applied to the humidifier, aerosol droplets of dissolved and suspended antimicrobial metals with atomic disorder were generated and flowed from the output nozzle.

A test chamber was constructed using a stainless steel frame with a transparent plastic covering. The frame was placed on a stainless steel plate. The output nozzle from the humidifier was modified so that the aerosol could be directed into the chamber at a height of approximately 30 cm from the base. The plates and other test samples were placed on the stainless steel plate and exposed to the aerosol for a prescribed length of time.

Solution 1

A solution of antimicrobial metals with atomic disorder was prepared by immersing 518 sq. inches of Acticoat® burn dressing in 1L of reverse osmosis water, which was treated with $CO_2$ to maintain a pH of 6.5. After 20 minutes the concentration of silver in the water was 85 $\mu$g/mL.

Solution 2

A solution containing 370 $\mu$g/mL of silver from a Acticoat® dressing was prepared as follows: 1 L of reverse osmosis water was purged with commercial grade carbon dioxide until the pH was 4.3. Sufficient Acticoat® dressing was added to bring the pH up to 6.5. At that time, the silver concentration was 370 $\mu$g/mL.

Solution 3

Ag as $AgNo_3$ was prepared by dissolving 0.157 g of $AgNo_3$ into 1 L of reverse osmosis water and mixed until dissolved. The solution was analyzed by Atomic Absorption Spectroscopy and found to be 102.9 ppm of silver.

Solution 4

Ag as $AgNO_3$ was prepared by dissolving 0.427 of $AgNO_3$ into 1 L of reverse osmosis water and mixed until dissolved. The solution was analyzed by Atomic Absorption Spectroscopy and found to be 295 ppm of silver.

Aerosolization

Petri dishes, containing Mueller Hinton agar, were streaked with 4 h old cultures of *Pseudomonas aeruginosa* or *Staphylococcus aureus*. The plates were then weighed and their exposed outer surfaces were coated with Parafilm to prevent condensation from occurring on these surfaces. These plates were placed in the aerosol chamber uncovered. The ultrasonic nebulizer was then started and run for 53 minutes. The plates were then removed from the chamber, the plastic was removed and the dishes re-weighed so that the amount of moisture loss/gain could be determined.

The plates were then placed in a 35° C. incubator for 16 h. After incubation the pattern and amount of growth was assessed on the plates for both organisms.

Viability Assessment

Three of the six plates made for each organism were tested to determine if the antimicrobial effect was cidal or static in nature. This was accomplished by rinsing or placing a piece of the clear section of agar in the Petri dish plates into Tryptic soy broth in a test tube and incubating for 4 h or 16 h. If the medium turned turbid in 4 h it would indicate that the antimicrobial affect was bacteriostatic in nature. If the organism took more than 16 h to grow, as indicated by turbidity, it was considered an indication that both static and cidal effects occurred. If no growth occurred, the effect was bactericidal.

Results

The results for Solutions 1 and 2 are summarized in Tables 1 and 2, respectively.

TABLE 1

Solutions 1 and 3 Results

| Organism | Antimicrobial Metals With Atomic Disorder | | $AgNo_3$ | |
|---|---|---|---|---|
| | Ps. Aeruginosa | S. aureus | Ps. Aeruginosa | S. aureus |
| Ag concentration (µg/mL) | 85 | 85 | 99 | 99 |
| pH of test solution | 6.5 | 6.5 | Approx. 6.5 | Approx. 6.5 |
| Exposure time (minutes) | 53 | 53 | 53 | 53 |
| Exposed area (sq. in) | 9.8 | 9.8 | 9.8 | 9.8 |
| Weight gain (g) | 0.8 | 0.8 | 1.05 | 1.05 |
| Growth at 16 h | 0 | 0 | 0 | ++++ |
| (0–++++) at 48 h | 0 | ++ | 0 | ++++ |
| Viable | | | | |
| 4 h | No | Yes | No | Yes |
| 16 h | Yes | Yes | Yes | Yes |

TABLE 2

Solutions 2 and 4 Results

| Organism | Antimicrobial Metals With Atomic Disorder | | $AgNo_3$ | |
|---|---|---|---|---|
| | Ps. aeruginosa | S. aureus | Ps. aeruginosa | S. aureus |
| Ag concentration (µg/mL) | 370 | 370 | 300 | 300 |
| pH of test solution | 6.5 | 6.5 | Approx. 6.3 | Approx. 6.3 |
| Exposure time (minutes) | 53 | 53 | 53 | 53 |
| Exposed area (sq. in) | 9.8 | 9.8 | 9.8 | 9.8 |
| Weight gain (g) | 1.14 | 1.14 | 1.12 | 1.12 |
| Growth at 16 h | 0 | 0 | 0 | 0 |
| (0–++++) at 48 h | 0 | 0 | 0 | +++ |
| Viable | | | | |
| 4 h | No | No | No | No |
| 16 h | No | No | No | N/A |

DISCUSSION

At the low concentration of silver in solution, the Acticoat® dressing generated silver was effective at controlling the growth of both organisms while the silver nitrate only prevented the growth of *Ps. aeruginosa*. Viability tests showed that at the low concentration, neither form of silver was completely bactericidal although the poor growth on the plates treated with antimicrobial metals with atomic disorder compared to the silver nitrate treated plates suggests that a significant log reduction occurred in the plates treated with the aerosol of antimicrobial metals with atomic disorder.

At a higher concentration of silver, both antimicrobial metals with atomic disorder (370 µg/mL) and $AgNo_3$ (300 µg/mL) were effective at controlling *P. aeruginosa*. Since no re-growth occurred, it is assumed that the agent at this concentration was bactericidal. Antimicrobial silver with atomic disorder was more effective than $AgNO_3$ at controlling *S. aureus*. No re-growth occurred on any plates or in the broth indicating a total kill of the organism while, in the $AgNO_3$ treatment, a large number of organisms grew at 16 h.

Based on weight gain during aerosol treatments, a dose per unit area can be calculated. In each case for Solution 1, the dose was 8.5 µg/sq. inch, while for Solution 2, the dose was 38 µg/sq. inch. These doses, on a per lung basis, would be less than 10 mg of silver per hour of treatment. Each hour of treatment with antimicrobial silver with atomic disorder aerosols appears to provide at least 48 h of protection. Therefore, the dose per day, from the high concentration treatment, would be about 5 mg or a little less than the silver released by 2 sq. inches of SSD per day.

The most significant advantage of using antimicrobial silver with atomic disorder may be the lack of a toxic action such as $NO_3$ or sulfadiazine.

Conclusions (1) Aerosols of antimicrobial metals with atomic disorder transmit the antimicrobial activity of the dressings to remote sites.

(2) Aerosols of antimicrobial metals with atomic disorder are more effective than comparable concentrations of silver nitrate.

(3) The dose delivered is acceptable and would not appear to be excessive.

(4) No toxic cations ($NO_3$ or sulfadiazine) are introduced to the patient.

EXAMPLE 7

Gels of Antimicrobial Metals With Atomic Disorder

Gel products of antimicrobial metals with atomic disorder encompass both "wet" and "dry" materials.

A "wet" gel product of antimicrobial metals with atomic disorder is a product that provides moisture to a dry skin condition (psoriasis, eczema, acne, wound, etc.) and facilitates autolytic debridement of necrotic tissue. It also delivers the antimicrobial and anti-inflammatory properties of the suspended antimicrobial metals with atomic disorder powders.

In many instances it is also beneficial to supply biologically active molecules to elicit a specific response such as cell migration, etc. Since these biologically active molecules are susceptible to microbial degradation if not protected, it is beneficial to include them in gels of antimicrobial metals with atomic disorder that will provide the necessary protection.

"Dry" gel products of antimicrobial metals with atomic disorder are physically stabilized (dry or cross-linked) materials that provide lubricious, antimicrobial, antithrombogenic, and anti-inflammatory properties to a variety of implantable, trancutaneous or topically applied devices. The coatings may also provide other benefits such as accelerating or otherwise facilitating tissue integration by creating a favorable environment for cell proliferation. This favorable environment may be created by including cytoconductive agents or anti-adhesion agents such as bone morphogenetic proteins, B-glucan hyaluronic acids in the gel. The gel may be stabilized by cross-linking the gel components (collagen, gelatin, etc.) or by drying the coated materials.

Examples of the primary gelling agents are listed in Table 3. Biologically active ingredients that may be used, in any combination with the primary gelling agents, are given in Table 4. Materials that should not be used with gels of antimicrobial silver with atomic disorder are given in Table 5.

TABLE 3

| Material | Percentage Composition |
| --- | --- |
| Carboxymethyl cellulose (CMC) | 0.1–10 |
| Polyvinyl alcohol (PVA) | 0.1–10 |
| Collagen | 0.1–10 |
| Pectin | 0.1–10 |
| Gelatin | 0.1–10 |
| Chitin | 0.1–10 |
| Chitosan | 0.1–10 |
| Alginate | 0.1–10 |
| Poly (α-amino acids) | |
| Polyester | |
| Poly-1-caprolactone | |
| PEG | |
| Cocoa butter | |
| Sepigel | |

TABLE 4

| Biologically Active Ingredients | Percentage Composition |
| --- | --- |
| Methyl paraben | <3 |
| Propyl paraben | <3 |
| B-glucan | <5 |
| Hyaluronic acid | <5 |
| Epidermal growth factor | <1 |
| Platelet derived growth factor | <1 |
| Transforming growth factor | <1 |
| Vascular endothelial growth factor | <1 |
| Interleukins | <1 |
| Heparin | <5 |
| Bone morphogenetic proteins | <1 |

TABLE 5

| Non-Compatible Materials | Percentage Composition |
| --- | --- |
| Chloride salts | >0.01 |
| Aldehydes | >0.01 |
| Ketones | >0.01 |
| Long chain alcohols | >0.01 |
| Glycerol | >0.01 |
| Triethanolamine | >0.01 |

EXAMPLE 8

Examples of Gels with Antimicrobial Metals With Atomic Disorder

No. 1

A commercial carboxymethyl cellulose/pectin gel (Duoderm Convatec) was combined with antimicrobial metals with atomic disorder powder to produce a gel with 0.1% silver. A logarithmic reduction test was performed as follows in the gel using *Pseudomonas aeruginosa*.

The inoculum was prepared by placing 1 bacteriologic loopful of the organism in 5 mL of trypticase soy broth and incubating it for 3–4 h. The inoculum (0.1 mL) was then added to 0.1 mL of gel and vortexed (triplicate samples). The mixture was incubated for one-half hour. Then 1.8 mL of sodium thioglycollate-saline (STS) solution was added to the test tube and vortexed. Serial dilutions were prepared on $10^{-1}$ to $10^{-7}$. A 0.1 mL aliquot of each dilution was plated in duplicate into Petri plates containing Mueller-Hinton agar. The plates were incubated for 48 h and then colonies were counted. Surviving members of organisms were determined and the logarithmic reduction compared to the initial inoculum was calculated.

The logarithmic reduction for this mixture was 6.2, indicating a significant bactericidal effect.

No. 2

Carboxymethyl cellulose (CMC) fibers were coated directly to produce a defective nanocrystalline antimicrobial coating. The CMC was then gelled in water by adding 2.9 g to 100 mL volume. This material was tested using the method of No. 1. The material generated a 5.2 logarithmic reduction of *Pseudomonas aeruginosa*, demonstrating that the gel had a significant bactericidal effect.

No. 3

An alginate fibrous substrate was directly coated with a defective nanocrystalline antimicrobial coating. The alginate (5.7 g) was added to 100 mL volume of water to create a gel.

This material was tested using the method of No. 1. The material generated a 5.2 logarithmic reduction of *Pseudomonas aeruginosa*, demonstrating that the gel had a significant bactericidal effect.

No. 4

A commercial gel containing CMC and alginate (Purilin gel Coloplast) was mixed with a defective nanocrystalline silver powder to give a product with 0.1% silver. This was tested as above with both *Pseudomonas aeruginosa* and *Staphylococcus aureus*. Zone of inhibition data was also generated for this gel as follows. An inoculum (*Pseudomonas aeruginosa* and *Staphylococcus aureus*) was prepared as in No. 1 and 0.1 mL of this was spread onto the surface of Mueller-Hinton agar in a Petri dish. A six mm hole was then cut into the agar at the center of the Petri dish and removed. The well was filled with either 0.1 mL of the silver containing gel, a mupirocin containing cream or a mupirocin containing ointment. The Petri plates were then incubated for 24 h and the diameter of the zone of inhibition was measured and recorded.

The silver containing gel produced 9 mm zones against both *Pseudomonas aeruginosa* and *Staphylococcus aureus*, while the mupirocin cream and ointment produced 42 and 48 mm zones against *Staphylococcus aureus* and 0 mm zones against *Pseudomonas aeruginosa*.

The silver containing gel reduced the *Pseudomonas aeruginosa* and *Staphylococcus aureus* properties 4.4 and 0.6 logs, respectively, showing good bactericidal activity. The mupirocin cream and ointment generated 0.4 and 0.8, and 0.8 and 1.6, log reductions against *Staphylococcus aureus* and *Pseudomonas aeruginosa*, respectively. The silver gel had both a greater bactericidal effect and spectrum of activity than the mupirocin containing products.

Nos. 5–10

The formula for Nos. 5–10 are summarized in Table 6. Zones of inhibitions were determined in No. 4 and log reductions were determined in No. 1.

All formulae provided a broader spectrum of activity and a greater bactericidal effect than did mupirocin in a cream or ointment form. The mupirocin cream produced zones of inhibition of 42 and 0, and log reduction of 0.4 and 0.8, against *Staphylococcus aureus* and *Pseudomonas aeruginosa*, respectively.

zones of 15 mm against both *Staphylococcus aureus* and *Pseudomonas aeruginosa*. Log reductions of 1.7 and >5 were produced against *Staphylococcus aureus* and *Pseudomonas aeruginosa*. This gel product had a greeted spectrum of activity than did mupirocin cream or ointment.

No. 12

A gel coat for a urinary catheter was prepared using the formula in No. 6. The coating was applied to the catheter using a dipping method. The coating was air dried overnight.

The dried gel coat was smooth and easy to handle. It was not tacky to touch and had excellent abrasion and adhesion properties. Upon rewetting, the surface became extremely slippery indicating excellent lubricious properties.

A zone of inhibition test was performed against *Pseudomonas aeruginosa* using an inoculum as prepared in No. 1. The inoculum (0.1 mL) was spread over the surface of Mueller-Hinton agar in a Petri plate. The catheter was cut into 1" segments which were laid on their side into the middle of the Petri plate. Petri plates were incubated for 24 h and then the zone of inhibitions was measured.

In all cases, zones of inhibition were generated that ranged from 7–10 mm. This indicates that getting drying and rehydrating had no negative effect on the antimicrobial activity of the gel coat.

What is claimed is:

1. A method for treating tissue, comprising:
    forming a solution at a site remote from the tissue which is to be treated by dissolving in water at least one antimicrobial metal with atomic disorder; and
    applying the solution in therapeutically effective amount to the tissue which is to be treated,
    wherein the tissue comprises at least one tissue selected from the group consisting of endocardium tissue, pericardium tissue, bone tissue, and joint tissue, and the at least one antimicrobial metal with atomic disorder has sufficient atomic disorder so that, when in contact with an alcohol or water-based electrolyte, said at least one antimicrobial metal with atomic disorder releases atoms, ions, molecules, or clusters of the at least one antimicrobial metal into the alcohol or water-based electrolyte on a sustainable basis.

2. A method according to claim 1 wherein the at least one antimicrobial metal is in nanocrystalline form.

3. A method according to claim 2 wherein the at least one antimicrobial metal is nanocrystalline silver.

TABLE 6

| No. | CMC | PVA | Antimicrobial Metals With Atomic Disorder[M] Powder | 0-glucan | Methyl Para-Ben | Propyl Para-ben | CZOI S. aureus | CZOI Ps. Aeruginosa | Log Reduction S. Aureus | Log Reduction Ps. Aeruginosa |
|---|---|---|---|---|---|---|---|---|---|---|
| 5 | 2% | | 0.1% | | | | 11 | 13 | 1.4 | >6 |
| 6 | 2% | 0.5% | 0.1% | | 0.1 | 0.02 | 14 | 15 | 3.3 | >6 |
| 7 | 2% | 0.5% | 0.1% | | | | 13 | 14 | 2.0 | N/A |
| 8 | 2% | 0.5% | 0.1% | | 0.1 | | 14 | 14 | 2.0 | N/A |
| 9 | 2% | 0.5% | 0.1% | | | 0.20 | 14 | 14 | 2.0 | N/A |
| 10 | 2% | 0.5% | 0.1% | 0.5 | 0.1 | 0.20 | 14 | 14 | 2.0 | >6 |

No. 11

A commercially available gel (glyceryl polymethacrylate) was blended with antimicrobial metals with atomic disorder powder to produce a gel with a silver content of 0.1%. This gel was tested as in Nos. 5–10 and was found to produce 4. A method according to claim 1 wherein the solution is applied by passing it through a catheter to the tissue which is to be treated.

5. A method according to claim 1 wherein the solution is applied by injection into the tissue which is to be treated.

6. A method according to claim 5 wherein injection is effected by the use of a needle.

7. A method according to claim 5 wherein injection is needle-less injection.

8. A method according to claim 1 wherein the solution is applied by injection into a body cavity so as to contact the tissue which is to be treated.

9. A method for treating tissue, comprising:

forming a solution at a site remote from the tissue which is to be treated by dissolving in water at least one noble metal with atomic disorder; and applying the solution in therapeutically effective amount to the tissue which is to be treated, wherein the tissue comprises at least one tissue selected from the group consisting of endocardium tissue, pericardium tissue, bone tissue, and joint tissue, and the at least one noble metal with atomic disorder has sufficient atomic disorder so that, when in contact with an alcohol or water-based electrolyte, said at least one noble metal with atomic disorder releases atoms, ions, molecules, or clusters of the at least one noble metal into the alcohol or water-based electrolyte on a sustainable basis.

10. A method according to claim 9, wherein the at least one noble metal is in nanocrystalline form.

11. A method according to claim 10, wherein the at least one noble metal is nanocrystalline silver.

12. A method according to claim 9, wherein the solution is applied by passing it through a catheter to the tissue which is to be treated.

13. A method according to claim 9, wherein the solution is applied by injection into the tissue which is to be treated.

14. A method according to claim 13, wherein injection is effected by the use of a needle.

15. A method according to claim 13, wherein injection is needle-less injection.

16. A method according to claim 9, wherein the solution is applied by injection into a body cavity so as to contact the tissue which is to be treated.

* * * * *

UNITED STATES PATENT AND TRADEMARK OFFICE
CERTIFICATE OF CORRECTION

PATENT NO. : 6,989,156 B2  Page 1 of 3
APPLICATION NO. : 10/128208
DATED : January 24, 2006
INVENTOR(S) : Gillis It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (0) days Delete the phrase "by 0 days" and insert -- by 25 days --

On the Title page; item [56] insert the following list of initialed cited prior art:

-- U.S. PATENT DOCUMENTS

| | | |
|---|---|---|
| 4,596,556 | 6/1986 | Morrow et al. |
| 4,790,824 | 12/1988 | Morrow et al. |
| 5,064,413 | 11/1991 | McKinnon et al. |
| 5,312,335 | 5/1994 | McKinnon et al. |
| Des. 349,958 | 8/1994 | Hollis et al. |
| 5,383,851 | 1/1995 | McKinnon, Jr. et al. |
| 5,399,163 | 3/1995 | Peterson et al. |
| 5,454,886 | 10/1995 | Burrell et al. |
| 5,520,639 | 5/1996 | Peterson et al. |
| 5,681,575 | 10/1997 | Burrell et al. |
| 5,753,251 | 5/1998 | Burrell et al. |
| 5,770,258 | 6/1998 | Takizawa |
| 5,837,275 | 11/1998 | Burrell et al. |
| 5,848,995 | 12/1998 | Walder |
| 5,899,880 | 5/1999 | Bellhouse et al. |
| 5,958,440 | 9/1999 | Burrell et al. |
| 5,965,610 | 10/1999 | Modak et al. |
| 5,985,308 | 11/1999 | Burrell et al. |
| 6,010,478 | 1/2000 | Bellhouse et al. |
| 6,013,050 | 1/2000 | Bellhouse et al. |

Signed and Sealed this

Sixth Day of July, 2010

David J. Kappos
*Director of the United States Patent and Trademark Office*

| | | |
|---|---|---|
| 6,017,553 | 1/2000 | Burrell et al. |
| 6,096,002 | 8/2000 | Landau |
| 6,238,686 | 5/2001 | Burrell et al. |
| 6,333,093 | 12/2001 | Burrell et al. |
| 2002/0051824 | 5/2002 | Burrell et al. |
| 2002/0192298 | 12/2002 | Burrell et al. |

FOREIGN PATENT DOCUMENTS

| | | |
|---|---|---|
| EP | 0328421 | 8/1999 |
| JP | 11124335 | 5/1999 |
| JP | 2000327578 | 11/2000 |
| WO | 93/23092 | 11/1993 |
| WO | 95/13704 | 5/1995 |
| WO | 00/27390 | 5/2000 |
| WO | 01/68179 | 9/2001 |
| WO | 01/80920 | 11/2001 |
| WO | 02/09729 | 2/2002 |

OTHER PUBLICATIONS

Derwent abstract, accession no. 1994-192726; abstracting DE 4302053 (1994)

Shigemasa et al., "Applications of Chitin and Chitosan for Biomaterials" Biotechnology & Genetic Engineering Reviews Vol. 13 (14) pp. 383-420

Thornton, "Deposition Technologies for Films and Coatings: Coating Deposition by Sputtering" Materials Science Series 5 pp. 170-243 1982

Thornton, "Influence of apparatus geometry and deposition conditions on the structure and topography of thick sputtered coatings" J. Vac. Sci. Technol., Vol. 11, No. 4, July/Aug. 1974

Tredget, "Evaluation of Wound Healing using Silver Dressing", February 22, 1996

Tredget et al., "A Matched-Pair, Randomized Study Evaluating the Efficacy and Safety of Acticoat* Silver-Coated Dressing for the Treatment of Burn Wounds," Journal of Burn Care & Rehabilitation November/December 1998; 19:531-7

Voigt, et al., "The Use of Acticoat as Silver Impregnated Telfa Dressings in a Regional Burn and Wound Care Center: The Clinicians View," Wounds, Volume 13, Number 2, March/April 2001, Supplement B; pp. 11-20

Wright et al., "Early healing events in a porcine model of contaminated wounds: effects of nanocrystalline silver on matrix metalloproteinases, cell apoptosis, and healing" Wound Repair and Regeneration 2002; 10:141-151

Wright, et al., " The Comparative Efficacy of Two Antimicrobial Barrier Dressings: In-vitro Examination of Two Controlled Release of Silver Dressings" Wounds Vol. 10, Number 6 November/December 1998, pp. 179-188

Wright, et al., "Efficacy of topical silver against fungal burn wound pathogens", AJIC Vol. 27, No. 4, August 1999

Wright, et al., "Wound Management in an era of increasing bacterial antibiotic resistance: A role for topical silver treatment," AJIC Vol. 26, No. 6; pp. 572-577 December 1998

Yin et al., "Comparative Evaluation of the Antimicrobial Activity of ACTICOAT* Antimicrobial Barrier Dressing" Journal of Burn Care & Rehabilitation, Vol. 20, Number 3 May/June 1999

Yin, et al., "Effect of Acticoat Antimicrobial Barrier Dressing on Wound Healing and Graft Take", Burn Care & Rehabilitation, part 2 Jan/Feb 1999 --